(12) United States Patent
Kumar et al.

(10) Patent No.: US 10,512,792 B2
(45) Date of Patent: Dec. 24, 2019

(54) AUTOMATIC PLAN OPTIMIZATION FOR CHANGING PATIENT ANATOMY IN THE PRESENCE OF MAPPED DELIVERED DOSE FROM DELIVERED FRACTIONS

(71) Applicant: KONINKLIJKE PHILIPS N.V., Eindhoven (NL)

(72) Inventors: Prashant Kumar, Bangalore (IN); Karl Antonin Bzdusek, Madison, WI (US); Vaitheeswaran Ranganathan, Bangalore (IN); Matthew Palmer, Houston, TX (US); Michael Kantor, Houston, TX (US)

(73) Assignees: KONINKLIJKE PHILIPS N.V., Eindhoven (NL); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 3 days.

(21) Appl. No.: 14/600,474

(22) Filed: Jan. 20, 2015

(65) Prior Publication Data
US 2015/0141733 A1    May 21, 2015

Related U.S. Application Data

(63) Continuation-in-part of application No. PCT/IB2013/059440, filed on Oct. 18, 2013.
(Continued)

(51) Int. Cl.
*A61N 5/10* (2006.01)
*G06F 19/00* (2018.01)
*G16H 20/40* (2018.01)

(52) U.S. Cl.
CPC ......... *A61N 5/1039* (2013.01); *A61N 5/1031* (2013.01); *A61N 5/1038* (2013.01);
(Continued)

(58) Field of Classification Search
CPC .. A61N 5/1031; A61N 5/1038; A61N 5/1039; A61N 5/1042; A61N 5/1045; A61N 5/1047; G06F 19/3481
See application file for complete search history.

(56) References Cited

U.S. PATENT DOCUMENTS

| | | | | |
|---|---|---|---|---|
| 7,369,645 | B2 * | 5/2008 | Lane | A61N 5/1031 378/65 |
| 7,574,251 | B2 * | 8/2009 | Lu | A61N 5/103 600/427 |

(Continued)

FOREIGN PATENT DOCUMENTS

| | | |
|---|---|---|
| JP | 2002210027 | 7/2002 |
| WO | 2011110958 | 9/2011 |

(Continued)

OTHER PUBLICATIONS

Bronnikov, A. V.; Reconstruction of Attenuation Map Using Discrete Consistency Conditions; 2000; IEEE Trans. on Medical Imaging; 19(5)451-462.

(Continued)

*Primary Examiner* — Wyatt A Stoffa

(57) ABSTRACT

A therapy planning system and method generate an optimal treatment plan accounting for changes in anatomy. Therapy is delivered to the subject according to a first auto-planned optimal treatment plan based on a first image of a subject. A second image of the subject is received after a period of time. The second image is registered with the first image to generate a deformation map accounting for physiological changes. The second image is segmented into regions of interest using the deformation map. A mapped delivered dose is computed for each region of interest using the dose delivery goals and the deformation map. The first treatment (Continued)

plan is merged with the segmented regions of the second image and the mapped delivered dose during optimization.

16 Claims, 3 Drawing Sheets

Related U.S. Application Data

(60) Provisional application No. 61/719,528, filed on Oct. 29, 2012.

(52) U.S. Cl.
CPC ......... *A61N 5/1045* (2013.01); *A61N 5/1047* (2013.01); *G06F 19/3481* (2013.01); *G16H 20/40* (2018.01); *A61N 5/1042* (2013.01)

(56) References Cited

U.S. PATENT DOCUMENTS

| | | | | |
|---|---|---|---|---|
| 7,831,289 | B2* | 11/2010 | Riker | A61N 5/1031 378/65 |
| 7,899,517 | B2* | 3/2011 | Kindlein | A61N 5/1031 600/1 |
| 8,222,616 | B2* | 7/2012 | Lu | A61N 5/103 250/390.03 |
| 9,586,058 | B2* | 3/2017 | Bert | A61N 5/103 |
| 2005/0111621 | A1* | 5/2005 | Riker | A61N 5/1031 378/65 |
| 2006/0293583 | A1* | 12/2006 | Saracen | A61N 5/1038 600/407 |
| 2007/0041495 | A1* | 2/2007 | Olivera | A61N 5/103 378/65 |
| 2007/0041497 | A1* | 2/2007 | Schnarr | A61N 5/103 378/65 |
| 2007/0043286 | A1* | 2/2007 | Lu | A61N 5/103 600/407 |
| 2007/0088573 | A1* | 4/2007 | Ruchala | A61N 5/103 705/2 |
| 2007/0189591 | A1* | 8/2007 | Lu | A61N 5/103 382/128 |
| 2008/0002811 | A1* | 1/2008 | Allison | A61N 5/103 378/65 |
| 2009/0110145 | A1* | 4/2009 | Lu | A61N 5/103 378/65 |
| 2011/0053564 | A1 | 3/2011 | Imaeda | |
| 2011/0112351 | A1* | 5/2011 | Fordyce, II | A61N 5/103 600/1 |
| 2011/0130614 | A1* | 6/2011 | Schulz | A61N 5/103 600/1 |
| 2012/0123184 | A1* | 5/2012 | Otto | A61N 5/1067 600/1 |
| 2012/0136677 | A1 | 5/2012 | Ziegenhein et al. | |
| 2015/0273238 | A1* | 10/2015 | Kumar | G06F 19/3481 600/1 |

FOREIGN PATENT DOCUMENTS

| | | | |
|---|---|---|---|
| WO | 2011154853 | A1 | 12/2011 |
| WO | 2012024448 | A2 | 2/2012 |
| WO | 2012045163 | A1 | 4/2012 |

OTHER PUBLICATIONS

Castadot, P., et al.; Adaptive Radiotherapy of Head and Neck Cancer; 2010; Semin. Radiat. Oncol.; 20:84-93.

Craft, D. L, et al.; Improved Planning Time and Plan Quality Through Multicriteria Optimization for Intensity-Modulated Radiotherapy; 2012; Int. J. Radiat. Oncol. Biol. Phys.; 82(1)83-90.

Defrise, M., et al.; Time-of-flight PET data determine the attenuation sinogram up to a constant; 2012; Physics in Medicine & Biology; 57(4)885-902.

Gopal, R., et al.; Plan space: representation of treatment plans in multidimensional space; 2002; Int'l. Journal of Radiation Oncology Biology Physics; 53(5)1328-1336.

Hamilton, R., et al.; Intensity Modulated Radiation Therapy: A Clinical Perspective; 2005; vol. 1, Chapt. 10 "Treatment Planning"; pp. 151.

Moore, K. L., et al.; Quantitative Metrics for Assessing Plan Quality; 2012; Semin. Radiat. Oncology; 22:62-69.

Natterer, F.; Computerized Tomography with Unknown Sources; 1983; SIAM Journal on Applied Mathematics; 43(5)1201-1212.

Nuyts, J., et al.; Simultaneous Maximum a Posteriori Reconstruction of Attenuation and Activity Distributions from Emission Sinograms; 1999; IEEE Trans. on Medical Imaging; 18(5)393-403.

Oelfke, U., et al.; Inverse Planning for Photon and Proton Beams; 2001; Medical Dosimetry; 26(2)113-124.

Petit, S. F., et al.; Increased organ sparing using shape-based treatment plan optimization for intensity modulated radiation therapy of pancreatic adenocarcinoma; 2012; Radiotherapy and Oncology; 102:38-44.

Rosen, I., et al.; Interactively exploring optimized treatment plans; 2005; Int'l. Journal of Radiation Oncology Biology Physics; 61(2)570-582.

Salomon, A., et al.; Simultaneous Reconstruction of Activity and Attenuation for PET/MR; 2011; IEEE Trans. on Medical Imaging; 30(3)804-813.

Welch, A., et al.; Attenuation Correction in PET Using Consistency Information; 1998; IEEE Trans. on Nuclear Science; 45(6)3134-3141.

Wu, B., et al.; Data-driven Approach to Generating Achievable Dose-Volume Histogram Objectives in Intensity-modulated Radiotherapy Planning; 2010; Int. J. Radiation Oncology Biol. Phys.; 79:1241-1247.

Wu, B., et al.; Knowledge-based and Patient-Geometry Specific IMRT Treatment; 2010; Med. Phys.; 37:3368.

Wu, B., et al.; Patient geometry-driven information retrieval for IMRT treatment plan quality control; 2009; Med. Phys.; 36(12)5497-5505.

Wu, B., et al.; Using overlap volume histogram and IMRT plan data to guide and automate VMAT planning; A head-and-neck case study; 2013; Medical Physics; 40(2)021714-1-7.

Zhang, H. H., et al.; Modeling Plan-Related Clinical Complications using Machine Learning Tools in a Multi-Plan IMRT Framework; 2009; Int. J. Radiat. Oncol. Biol. Phys.; 74(5)1617-1626.

Zhang, X., et al.; A sensitivity-guided algorithm for automated determination of IMRT objective function parameters; 2006; Med. Phys.; 33(8)2935-2944.

\* cited by examiner

AUTOMATIC PLAN OPTIMIZATION FOR CHANGING PATIENT ANATOMY IN THE PRESENCE OF MAPPED DELIVERED DOSE FROM DELIVERED FRACTIONS

This application is a continuation-in-part of PCT/IB2013/059440, filing date Oct. 18, 2013 (WO 2014/068435 publication date May 8, 2014), and U.S. Ser. No. 61/719,528 filed Oct. 29, 2012.

FIELD

The present application relates generally to radiation therapy. It finds particular application in conjunction with radiation therapy planning and will be described with particular reference thereto. However, it is to be understood that it also finds application in other usage scenarios and is not necessarily limited to the aforementioned application.

BACKGROUND

In radiation therapy planning, creating a patient specific treatment plan can be a time consuming and tedious task. Many of the steps are redundant and vary little from patient to patient or plan to plan. Many of these steps can be automated using macro languages or scripts, but certain aspects are difficult without tools for writing logical expressions, loops, and other common programming functionality.

One area that is difficult to automate in current treatment planning is intensity-modulated radiation therapy (IMRT) or volumetric-modulated arc therapy (VMAT) optimization. Optimization is an iterative process where a user attempts to specify planning goals in the form of dose or biological objectives to create an ideal dose to target structures, typically a uniform dose, and minimize the dose to critical structures.

For a plan with many target and critical structures, the optimization problem has a large number of dimensions that is difficult for a user to navigate. Further, current user interfaces can contain long lists of goals for a user to control. However, only a small subset are necessary, and many can be hidden or grouped together into common goals. Even more, while it is relatively easy to create a plan that meets the goals, it is typically difficult to create an optimal plan. Plans can typically be further optimized, usually significantly, but an optimal plan is hard to define. Therefore it is hard to judge the degree of optimization in the current trial. Either additional structures can be considered or dose to existing critical structures can be further reduced. Hence, optimization can be tedious, inconsistent, non-optimal, and non-intuitive.

Intensity-modulated radiation therapy (IMRT) plans and Volumetrically Modulated Arc Therapy (VMAT) plans are typically based on a pre-treatment computed tomography (CT) scan that provides a snapshot of the patient's anatomy. However, inter-fractional patient variations may occur because of anatomical modifications. Therefore, the accuracy of IMRT/VMAT delivery may be compromised during the treatment course, potentially affecting the therapeutic index and normal tissue/organ sparing. Hence, adapting the plan for the changing anatomy may be useful in delivering high quality treatment to cancer patients.

Several tools for creating adaptive and/or composite plans are available in commercial treatment planning systems. Similarly various systems for automatic planning have been proposed and some have recently been commercialized. These tools can combine the dose from multiple plans and prescriptions using rigid and deformable transforms creating an accumulated dose. Some of these tools can even optimize a plan using an "accumulated" dose using standard IMRT optimization. However, none of these systems use an objective tuning or auto-planning system to re-optimize based on accumulated dose.

Optimization based on accumulated dose has inherent problems in standard optimization solved by auto-planning. The optimization problem has a large number of dimensions that is difficult for a user to navigatem, in particular for a plan with many target and critical structures. Further, current user interfaces can contain long lists of goals for a user to control. However, only a small subset is necessary, and many can be hidden or grouped together into common goals. While it is relatively easy to create a plan that meets the goals, it is difficult to create an optimal plan. Plans can be further optimized, usually significantly, but an optimal plan is hard to define. Therefore, it is hard to judge the degree of optimization in the current trial. Either additional structures can be considered or dose to existing critical structures can be further reduced. Hence, optimization can be tedious, inconsistent, non-optimal, and non-intuitive.

SUMMARY

The present application provides a new and improved system and method which overcome the above-referenced problems and others.

The present application presents an automatic plan optimization approach addressing dynamic planning arising from changes in a patient's anatomy during the course of treatment. The proposed methodology achieves an optimal plan for future prescription(s) by automatically factoring in the dose which got delivered from the previous fractions. In the context of changing patient anatomy, the discussed methodology automatically computes an optimal plan on the patient's secondary image by factoring in the dose delivered with the initial plan on the patient's primary image. The process is driven by a treatment technique template, i.e. clinical goals and priorities, used generate the auto-plan on the patient's primary image. It is achieved by combining an auto-planning solution with deformable image registration based dynamic planning capability.

In accordance with one aspect, a therapy planning system for generating an optimal treatment plan, said system comprising at least one processor programmed to: receive a secondary image of the subject after delivery of therapy to the subject according to a first treatment plan based on a primary image over a period of time. The system accounts for differences between the primary image and the secondary image and computes a mapped delivered dose for the secondary image. The system generates a second treatment plan based on the differences and the mapped delivered dose.

In accordance with another aspect, a therapy planning method for generating an optimal treatment plan, said method includes receiving a secondary image of the subject after delivering therapy to a subject according to a first treatment plan based on a primary image over a period of time. The method includes accounting for differences between the primary image and the secondary image and computing a mapped delivered dose for the secondary image. The method includes generating a second treatment plan based on the differences and the mapped delivered dose.

In accordance with another aspect, a therapy planning system for generating an optimal treatment plan, said system comprising at least one processor programmed to: generate a first optimal treatment plan based on first imaging data of a subject using an auto-planning technique, the optimal treatment plan including dose delivery goals and deliver therapy to the subject according to the optimal treatment plan and the dose delivery goals over a period of time. The system receives second imaging data of the same subject at the end of the period of time and deformably registers the second imaging data with the first imaging data to generate a deformation map accounting for physiological changes in the second imaging data with respect to the first imaging data. The system segments the second imaging data into regions of interest using the deformation map and/or others segmentation methods and computes a mapped delivered dose for each region of interest using the dose delivery goals of the first optimal treatment plan and the deformation map. The system merges the first optimal treatment plan with the segmented regions of interest of the second imaging data and the mapped delivered dose. The system generates a second optimal treatment plan according to an auto-planning technique wherein the merged data is used as the initial start point.

One advantage resides in a more intuitive user interface for radiation therapy planning.

Another advantage resides in a more optimized radiation therapy plan.

Another advantage resides in less tedious radiation therapy planning.

Another advantage resides in more consistent radiation therapy planning.

Another advantage resides in lower patient doses.

Still further advantages of the present invention will be appreciated to those of ordinary skill in the art upon reading and understand the following detailed description.

BRIEF DESCRIPTION OF THE DRAWINGS

The present application may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
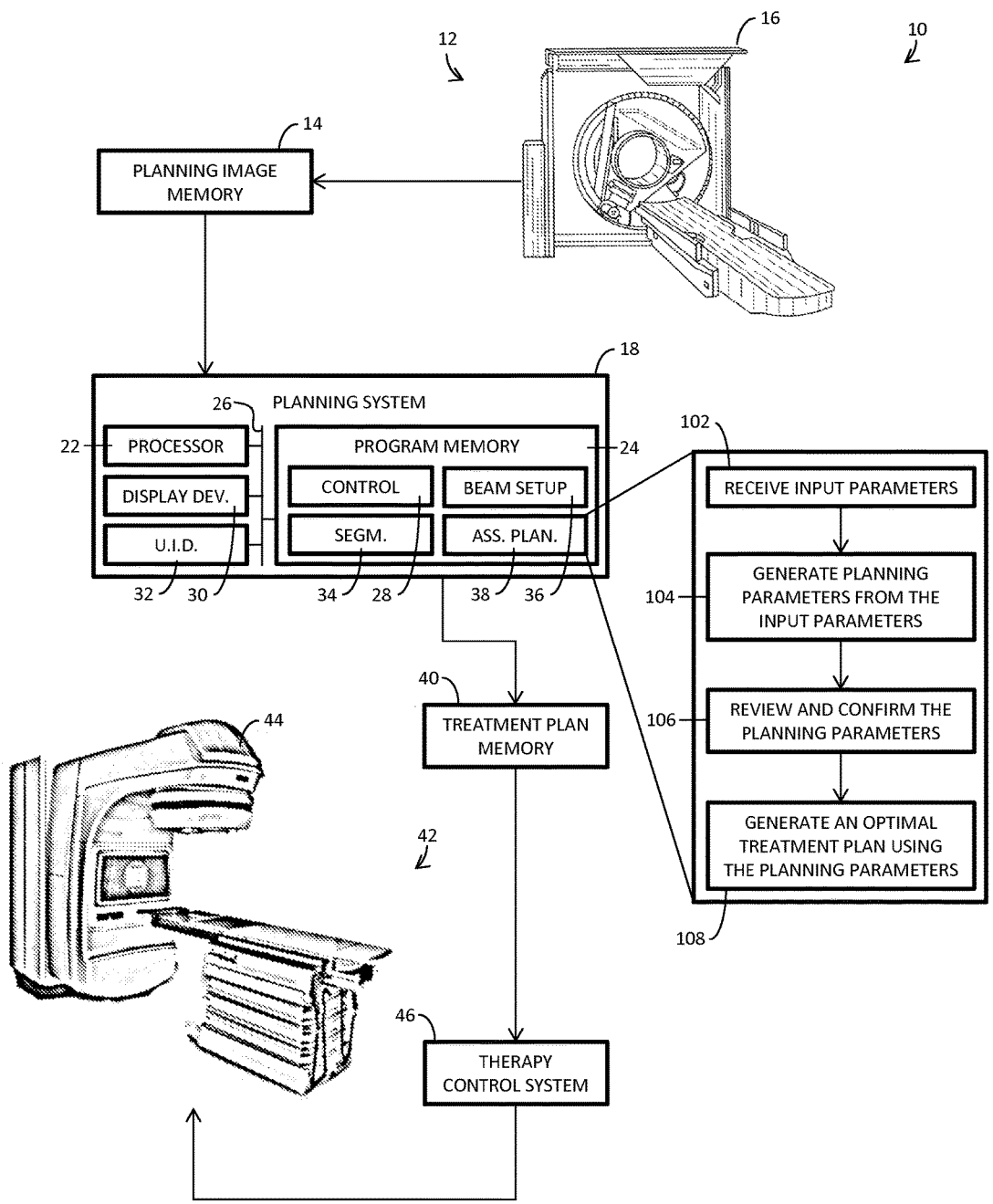
FIG. 1 illustrates a therapy system including an improved method for generating treatment plans.

With reference to FIG. 1, a therapy system 10, such as an intensity-modulated radiation therapy (IMRT) system or a volumetric-modulated arc therapy (VMAT) system, includes an imaging system 12 to generate one or more planning images of a region of interest of a patient. The planning images are volumetric (i.e., three-dimensional) and typically stored in a planning image memory 14 of the therapy system 10. The region of interest includes one or more target structures and, typically, one or more critical structures. Each of the target structures is a lesion or other tissue region, such as a tumor, to be irradiated. Each of the critical structures is an organ or other tissue region which is at risk of damage from the radiation intended for the target structures, such as radiation traveling to the target structures, which has passed through the target structures, or which passes closely adjacent the target structures.

The imaging system 12 generates the planning images using one or more imaging modalities, such as computed tomography (CT), positron emission tomography (PET), magnetic resonance (MR), single photon emission computed tomography (SPECT), cone-beam computed tomography (CBCT), and the like. Hence, the imaging system 12 includes one or more scanners 16 corresponding to the imaging modalities, as well as a backend system reconstructing raw image data from the scanners into the planning images. As illustrated, the imaging system 12 generates the planning images using at least CT and includes a CT scanner 16.

A planning system 18 of the therapy system 10 generates an optimal treatment plan for the patient on the planning images, which are typically received from the planning image memory 14. The optimal treatment plan suitably includes a plurality of treatment fractions, each identifying planning target volumes (PTVs) for the target structures, margins around the target structures, dose profiles for the target structures, dose limits for the critical structures, and therapy beam directions and intensities, and is typically stored in a treatment plan memory 20 of the therapy system 10. The planning system 18 includes at least one processor 22 and at least one program memory 24. The program memory 24 includes processor executable instructions that, when executed by the processor 22, generate the optimal treatment plan. The processor 22 executes the processor executable instructions to generate the optimal treatment plan. The planning system 18 further includes at least one system bus 26 interconnecting the processor 22, the program memory 24, and any other components of the planning system 18.

A control module 28 of the processor executable instructions controls overall operation of the planning system 18, including generation of the optimal treatment plan. The control module 28 suitably displays a graphical user interface (GUI) to a user of the planning system 18 using a display device 30 of the planning system 18. Further, the control module 28 suitably allows the user to interact with the GUI using a user input device 32 of the planning system 18. For example, the user can interact with the GUI to specify parameters controlling the generation of the optimal treatment plan.

A segmentation module 34 of the processor executable instructions segments the planning images to identify the boundaries of the structures (i.e., the target structures and, typically, the critical structures) and bone or other radiation attenuating structures within the planning images. The segmentation can be performed automatically and/or manually. As to automatic segmentation, a segmentation routine is employed to identify the boundaries of the structures. The segmentation routine can be one of any number of known segmentation routines, such as a model or atlas based segmentation routine. As to manual segmentation, a user uses the user input device 32 to identify the boundaries of the structures. In some embodiments, the segmentation module 34 employs the user interface to display the planning images to the user. The user can then identify the boundaries of the structures on the planning images using the user input device 32.

It is also contemplated that the segmentation can be performed using a combination of automatic and manual segmentation. Namely, the boundaries of the structures can be automatically identified as described above. The automatically identified boundaries can then be displayed to the user, optionally overlaid on the planning images, using the display device 30 and the user can modify the identified boundaries, as necessary, using the user input device 32.

A therapy beam setup module 36 of the processor executable instructions configures one or more therapy beams used for therapy delivery. This can be performed automatically and/or manually. As to automatic therapy beam setup, an appropriate routine is employed to automatically configure parameters configuring the therapy beam. As to manual segmentation, a user uses the user input device 32 to specify parameters configuring the therapy beams. It is also contemplated that therapy beam setup can be performed using a combination of automatic and manual therapy beam setup. Namely, automatic selection can be employed, as described above. The automatically configured parameters can then be displayed to the user using the display device 30 and the user can modify the parameters, as necessary, using the user input device 32.

An auto-planning module 38 of the processor executable instructions generates the optimal treatment plan. This includes receiving 102 input parameters for generation of the treatment parameter. The input parameters include the boundaries of the structures (i.e., the target structures and, typically, the critical structures) within the planning images, which are identified using the segmentation module 34, as well as therapy beam configuration parameters, which are determined using the therapy beam setup module 36.

The input parameters further include parameters received from the user input device 32. These parameters include labeling each of the structures identified in the planning images as one of a target structure and a critical structure. Further, these parameters include, for each structure, specification of: 1) a dose profile to be achieved based on the user's expertise or clinical guidelines; and 2) a priority relative to the other structures. The priority of a structure indicates the priority of its corresponding dose profile relative to the other structures. The priorities can then be employed to resolve a conflict between, for example, covering a target structure and sparing a critical structure.

Figure 2:
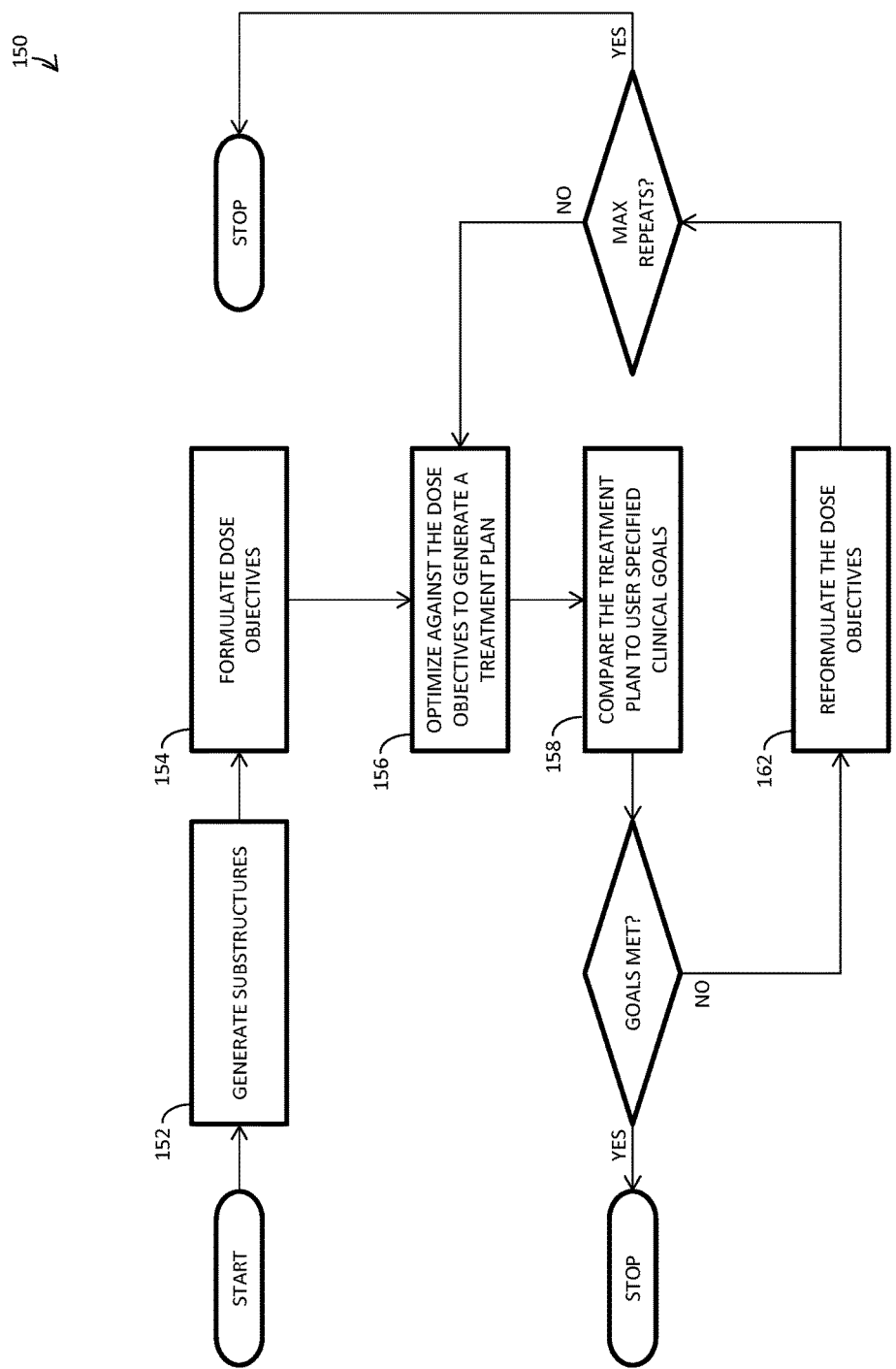
FIG. 2 illustrates a treatment plan generation routine.

Based on the input parameters, the auto-planning module 38 automatically generates 104 planning parameters to control a treatment plan generation routine 150, discussed hereafter and illustrated in FIG. 2. The planning parameters include, for example, iso-center, dose grid, optimization objectives, and so on.

In some embodiments, the user reviews and confirms 106 the planning parameters using the user input device 32. Namely, the planning parameters are displayed to the user using the display device 30. The user can then modify the planning parameters using the user input device 32 as necessary. Additionally, or alternatively, overlap statistics describing overlap between the structures are displayed to the user using the display device 30. The overlap statistics can assist the user in making priority decisions, such as, for example, the decision to spare a structure or sacrifice it for target coverage.

Overlap between structures is determined based on the input parameters using any number of approaches. According to one approach, volumetric overlap between the structure and the other structure is determined, the volumetric overlap corresponding to the overlap region. According to another approach, a projection image of the structure and the other structure from the perspective of one of the therapy beams is created. The overlap between the structure and other structure is then determined within the projection image and the overlap region is back projected to the volumetric planning images. In some embodiments, this approach is employed for each therapy beam.

Based on the planning parameters (as confirmed, where applicable), the auto-planning module 38 generates 108 the optimal treatment plan according to the treatment plan generation routine 150 illustrated in FIG. 2. As will be seen, the treatment plan generation routine 150 progressively refines a set of dose objectives to drive an inverse planning optimization towards the optimal solution in a complex multi-dimensional search space. The optimal treatment plan is typically stored in a treatment plan memory 40 of the therapy system 10.

With further reference to FIG. 2, the treatment plan generation routine 150 includes generating 152 an optimal set of substructures from the structures identified in the planning images. The substructures are based on the geometrical relationship and relative priorities of the structures, and advantageously help the optimization run with as few conflicts as possible and achieve a faster convergence.

To generate the substructures, each structure is analyzed for overlap with other structures using any number of approaches, such as one or more of the approaches discussed above. For each overlap between the structure and another structure, the overlap region is removed from the structure to create a substructure if the priority of the structure is less than the priority of the other structure. For example, if a critical structure overlaps with a target structure having a higher priority, a substructure is generated, the substructure being the critical structure less the overlapping region. A padding margin can be removed from each of the substructure to account for the high dose gradient at the overlapping boundaries of the structures.

After generating the optimal set of substructures, dose objectives are formulated 154 using the structures and the substructures. Each dose objective includes a plurality of parameters, including a dose, a weight, biological factors, such as "a" value, and the like. Typically, the translation from user input goals to dose objectives for the optimizer is performed intelligently based on the dose profiles of the structures and substructures. However, the translation to dose objectives for the optimizer can also be performed intelligently based on distance profiles between the target and critical structures and substructures. The weights of the dose objectives are assigned based on the priority of the corresponding structures and substructures.

The dose profiles and priorities of the structures are incorporated into, or otherwise defined by, the planning parameters, and the substructures assume the dose profiles and priorities of the corresponding structures. Further, the distance profiles between target and critical structures and substructures are defined by the planning parameters or automatically.

Using the dose, biological, or other objectives, inverse planning optimization is performed 156 to generate a treatment plan. The inverse planning optimization routine can be any number of well-known routines. The goal is to reduce the dose to the critical structures and other non-target structures to a point just before significant coverage of the target structures is compromised, while maintaining intended dose coverage of the target structures.

The inverse planning optimization routine includes determining a tuning force for each of the dose objectives. The tuning force is based on one or more of the dose, the weight, the current value (i.e., an objective assessment against the optimizer's solution), and any number of biological parameters, such as "a" value. If the tuning force corresponds to a critical structure, the tuning force pushes the dose of the corresponding region towards a lower level. However, if the tuning force corresponds to a target structure, the tuning force pushes the dose of the corresponding region towards the dose profile of the target structure.

After the treatment plan is generated, the treatment plan is compared 158 to the user specified clinical goals, such as the dose profiles of the structures or heterogeneity indexes, to quantitatively assess how well the treatment plan achieves the clinical goals. The comparison and quantitative assessment can, for example, be performed by a scoring routine designed to score how well the treatment plan achieves the clinical goals. The clinical goals are incorporated into, or otherwise defined by, the planning parameters. A determination 160 is then made as to whether the clinical goals are met based on the comparison 158.

Even if the treatment plan and the clinical goals exceed a predetermined level, it may be possible to push the plan beyond the clinical goals by reformulating the dose objectives 162.

Reformulating the dose objectives guides towards an optimal solution (as per the user priority) by driving the tuning forces while maintaining a state of equilibrium. If a critical structure does not overlap with a target structure, the tuning force of the corresponding dose objective is adjusted towards a lower dose. Otherwise, the tuning force is adjusted based on the priority of the critical structure and clinical guideline requirements to achieve the optimal trade-off.

To reformulate the dose objectives, the current value of each of the objective functions is determined. As noted above, the current value is an objective assessment against the optimizer's solution (i.e., the treatment plan). The current value is compared to a predetermined convergence value, for example, specified by the user using the user input device. If the current value is less than the predetermined convergence value, the parameters of the dose objective are modified to increase the current value of the dose objective to approximately the predetermined convergence value. If the current value is greater than the predetermined convergence value, the parameters of the dose objective are modified to decrease the current value of the dose objective to approximately the predetermined convergence value.

In addition to modifying the parameters of the dose objectives, additional dose objectives can be added for high priority structures and/or the weights of existing objectives can be adjusted. For example, a high weight objective can be added for a high priority structure if the corresponding clinical goal is not met. As another example, hot and/or cold spots can be identified and objectives corresponding to these spots can be added to achieve a conformal dose distribution to target structures. As another example, dose spillage outside of target structures can be identified and objectives can be added to reduce the identified spillage.

In some embodiments, a user can employ the user input device 32 to modify the parameters of the dose objectives and/or generate new dose objectives. For example, the user can be presented with the objectives with the display device 30. The user can then modify the objectives manually using the user input device 32. As another example, the user can be presented with an abstracted user interface with the display device 30 which presents conflicting structure pairs. For each structure pair, the user can then specify priorities between the structures, which can be used to update the parameters of the dose objectives, using the user input device 32.

After reformulating the dose objectives, the foregoing actions, beginning with the performing 156 inverse planning optimization, are repeated for the reformulated dose objectives. In some embodiments, this repeating is performed for up to a predetermined number of times, such that a determination 162 is made as to whether the repeating has been performed more than the predetermined number of times before repeating. Insofar as it has, the optimal treatment plan is the most recent treatment plan. Otherwise, the repeating continues. Alternatively, the repeating is performed until the plan change from one repetition to the next falls below a minimum improvement criteria.

Referring to FIG. 1, a delivery system 42 executes the optimal treatment plan to deliver therapy, such as ablation therapy, external beam radiation therapy and/or brachytherapy, to the patient. The therapy typically includes radiation, such as one or more of x-rays, protons, high-intensity focused ultrasound (HIFU), and the like. The delivery system 42 includes a delivery apparatus 44, such as a linear particle accelerator, and a control system 44, which controls the delivery apparatus 46 in accordance with the optimal treatment plan. The optimal treatment plan is typically received from the treatment plan memory 40, but other sources are contemplated.

Figure 3:
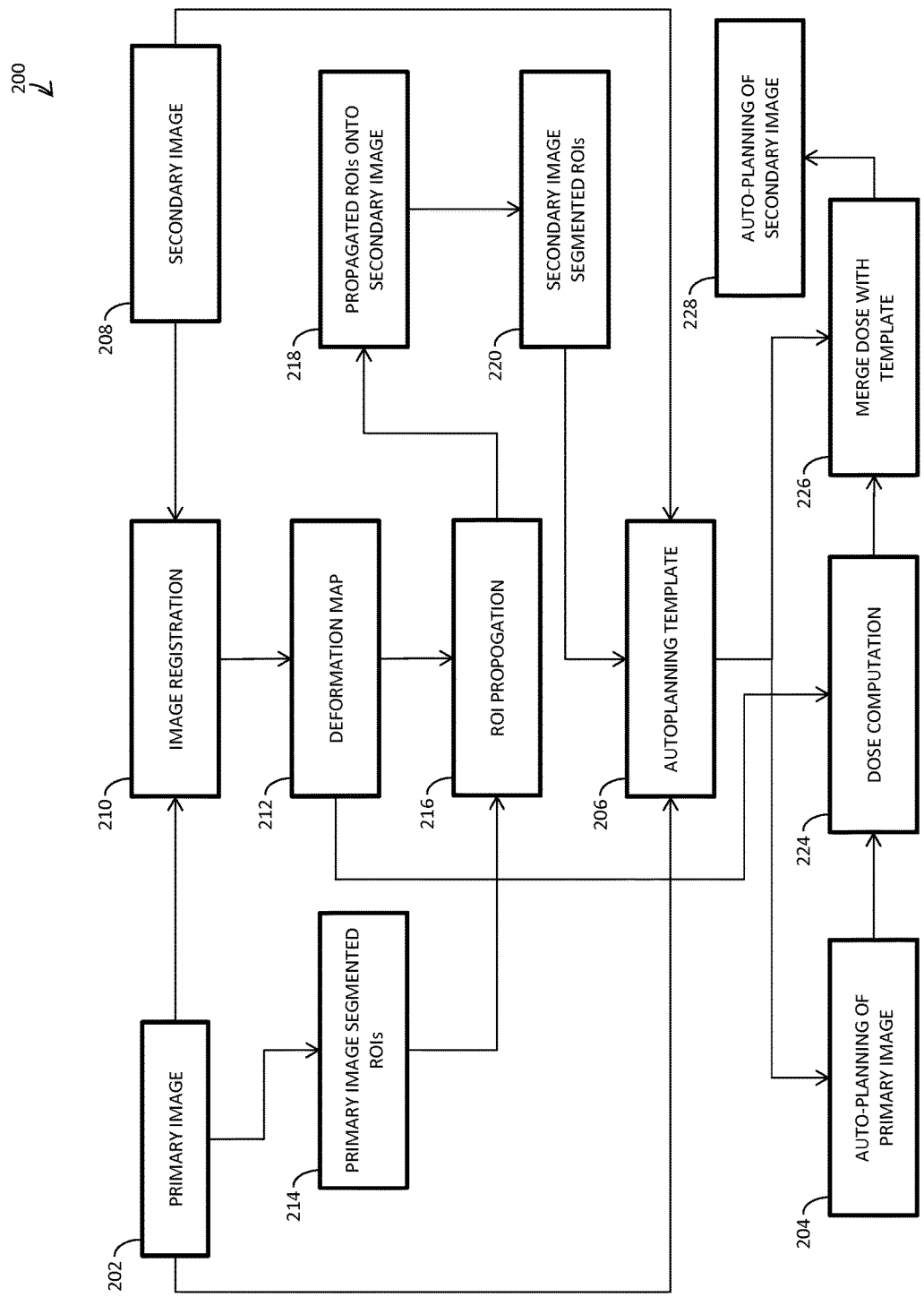
FIG. 3 illustrates treatment plan generation for changed anatomy in a secondary image.

After delivery of therapy to the patient, the delivered dose to the patient can affect the physiological structure within the patient, e.g. a shrunken tumor. In the case the patient physiology changes, the optimal treatment plan obtained as described above will sometimes be less than optimal for the changed physiology. With reference to FIG. 3, a flow chart 200 for accounting for delivered dose and changed patient physiology is depicted. A primary image 202 of the patient is the initial image of the patient before any dose has been delivered. An optimal treatment plan of the primary image 202 is generated 204 as described above using the autoplanning template 206. The optimal treatment plan is used in treating the patient with the delivery apparatus 44.

The patient receives treatment according to this initial treatment plan for a period of time, after which secondary images 208 of the patient are generated. The secondary images 208 are registered 210 using an image registration technique with the primary images 202. The image registration 210 uses a rigid image registration and non-rigid registration to estimate the mapping between the primary and secondary images 202, 208.

From the registered images, the a deformation map 212 representing the physiological or anatomical changes between the primary and secondary images 202, 208 is determined. The primary and secondary images, generated at two different times respectively, are used in generating deformation maps, which describe the deformations that transform or deform the primary image generated at one time into a common coordinate system and registered with the secondary image taken at a different time.

Modeling anatomical shape change as deformation, such as by a deformation map, uses landmarks, features, surfaces, and the like in three dimensions (3D) to define a mapping (transformation) between two images or sets of images (e.g., of the same anatomy) into the same coordinate frame or frame of reference. Various algorithms are available for performing these mappings or transformations among sets of images. Once landmark and/or features and/or surfaces are identified and paired between the images, these points are used to compute a coordinate transformation that maps every coordinate location in one image to a corresponding location in the other image and align them accordingly into one coordinate system, i.e. image registration 210.

The deformation map 212 aids a ROI propagation technique 214. The ROI propagation 214 uses the deformation map 212 to segment the secondary image 208 into segmented ROIs using the segmented ROIs of the primary image 216. The deformation map is applied to the segmented ROIs of the primary image 216 which results in propagated ROIs in the secondary image 218. In one embodiment, the user corrects the propagated ROIs to define the desired target and organs at risk to form segmented ROIs of the secondary image 220.

The secondary image 208 and the segmented ROIs of the secondary image 220 are input into the auto-planning template 206. The template 206 includes initial plan parameters such as clinical goals and priorities for the ROIs and initial beam placements. The template 206 maps the plan parameters to the segmented ROIs of the secondary image 220.

The deformation map 212 is used in computing a mapped delivered dose 224 for the secondary image 208. During the dose computation 224, first the delivered dose for the ROIs of the primary image is received. In one embodiment, the recommended dose of the optimal treatment plan of the primary image is used as the delivered dose. In another embodiment, the actual dose delivered to the patient is received through the user input 32. The delivered dose is applied to the deformation map 212 to compute the mapped delivered dose 224, i.e. the dose given to each ROI in the secondary image that has already been delivered to the patient.

In one embodiment, the computed mapped delivered dose 224 is merged 226 with the plan parameters from the template 206 to during optimization of a treatment plan based on the secondary image. The secondary image is optimized according to the iterative process described above and depicted in FIG. 2 to create an updated optimal treatment plan that accounts for the changed physiology of the patient depicted in the secondary image and the already delivered radiation dose, i.e. the mapped delivered dose, to the patient. The updated optimal treatment plan can be delivered to the patient using the delivery system 42 including the delivery apparatus 44 and the control system 46.

In another embodiment, optimization of the secondary image is performed using the propagated ROIs resulting in a secondary dose profile. After the optimization, the computed mapped delivered dose is merged with the secondary dose profile to take into account the previous delivered dose.

In another embodiment, the computed mapped delivered dose 224 and actual delivered dose are stored and used for future auto-plans.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A therapy planning system for generating an optimal treatment plan, said system comprising:
   at least one processor programmed to:
     receive a secondary image of a subject after delivery of therapy to the subject according to a first treatment plan based on a primary image over a period of time;
     account for differences between the primary image and the secondary image by registering the secondary image with the primary image;
     compute a mapped delivered dose for the secondary image, including the at least one processor further programmed to:
       receive a plurality of delivered dose values given to the subject according to the first treatment plan; and
       apply the deformation map transform to the delivered dose values to compute at least one mapped delivered dose value associated with the secondary image;
     generate a second treatment plan based on the differences and the mapped delivered dose;
   wherein the registration of the secondary image and the primary mage includes the processor programmed to:
     generate a deformation map representing anatomical differences between the primary image and the secondary image including transforms converting the primary image into the secondary image;
   wherein the at least one processor is further programmed to:
     generate the first treatment plan including a plurality of treatment plan parameters of a plurality of objectives; and
     reformulate the plurality of objectives including both (i) modifying the parameters of the plurality of objectives and (ii) adding one or more additional objectives to the plurality of objectives to reduce an identified dose spillage outside of a target structure.

2. The therapy planning system according to claim 1, wherein:
   the plurality of objectives include a dose objective; and
   the reformulating the plurality of objectives includes adjusting the dose objective towards a lower dose.

3. The therapy planning system according to claim 1, wherein the at least one processor is further programmed to:
   adjust the first treatment plan based on the reformulated plurality of objectives to generate the second treatment plan by using a tuning force to reduce a dose to a critical structure.

4. The therapy planning system according to claim 3, wherein the at least one processor is further programmed to:
   account for the mapped delivered dose values during the adjustment of the first treatment plan.

5. The therapy planning system according to claim 3, wherein the at least one processor is further programmed to:
   account for the mapped delivered dose values after the adjustment of the first treatment plan.

6. A therapy planning system for generating an optimal treatment plan, said system comprising:
   at least one processor programmed to:

receive a secondary image of a subject after delivery of therapy to the subject according to a first treatment plan based on a primary image over a period of time;
account for differences between the primary image and the secondary image;
compute a mapped delivered dose for the secondary image; and
generate a second treatment plan based on the differences and the mapped delivered dose;
wherein the at least one processor is further programmed to account for the differences between the primary image and the secondary image by:
registering the secondary image with the primary image;
wherein the registration of the secondary image and the primary image includes the at least one processor programmed to:
generate a deformation map representing anatomical differences between the primary image and the secondary image including transforms converting the primary image into the secondary image;
wherein the at least one processor is further programmed to:
segment the secondary image into regions of interest by applying the deformation map transforms to previously segmented regions of interest in the primary image;
apply an auto-planning template previously generated for the primary image to the segmented regions of interest of the secondary image, the template including initial plan parameters and objectives; and
reformulate the objectives including adding one or more additional objectives to the objectives to reduce an identified dose spillage outside of a target structure.

7. The therapy planning system according to claim 6, wherein the at least one processor is further programmed to adjust the first treatment plan based on the reformulated plurality of objectives to generate the second treatment plan by:
using a tuning force corresponding to a target structure to push a dose to a target structure towards a dose profile of the target structure.

8. The system of claim 6, wherein the at least one processor is further programmed to:
resolve a conflict between a target structure and a critical structure as part of generating the second treatment plan.

9. A therapy planning method for generating an optimal treatment plan, said method comprising, with one or more processors:
receiving a secondary image of a subject after delivering therapy to a subject according to a first treatment plan based on a primary image over a period of time;
accounting for differences between the primary image and the secondary image;
computing a mapped delivered dose for the secondary image;
generating a second treatment plan based on the differences and the mapped delivered dose;
registering the secondary image with the primary image, including:
generating a deformation map representing anatomical differences between the primary image and the secondary image including transforms converting the primary image into the secondary image;
wherein computing the mapped delivered dose includes, with the one or more processors:
receiving a plurality of delivered dose values given to the subject according to the first treatment plan; and
applying the deformation map transform to the delivered dose values to compute a mapped delivered dose value associated with the secondary image;
wherein the method further includes:
generating the first treatment plan including a plurality of treatment plan parameters of a plurality of objectives from an auto-planning template; and
reformulating the plurality of objectives including both: (i) modifying parameters of the plurality of objectives and (ii) adding one or more additional objectives to the plurality of objectives by identifying a spot, and adding an objective corresponding to the identified spot to achieve a conformal dose distribution to target structures.

10. A non-transitory computer readable medium carrying software which controls one or more processors to perform the method according to claim 9.

11. The therapy planning method according to claim 9, further including:
adjusting the first treatment plan based on the reformulated plurality of objectives to generate the second treatment plan by using a tuning force to reduce a dose to a critical structure.

12. The therapy planning method according to claim 9, further including:
controlling a therapy delivery apparatus to deliver therapy to a patient based on the computed, mapped delivered dose.

13. The therapy planning method according to claim 11, further including:
accounting for the mapped delivered dose values during the adjusting of the first treatment plan.

14. The therapy planning method according to claim 11, further including:
accounting for the mapped delivered dose values after the adjusting of the first treatment plan.

15. A therapy planning method for generating an optimal treatment plan, said method comprising:
receiving a secondary image of a subject after delivering therapy to a subject according to a first treatment plan based on a primary image over a period of time;
accounting for differences between e primary image and the secondary image;
computing a mapped delivered dose for the secondary image;
generating a second treatment plan based on the differences and the mapped delivered dose;
registering the secondary image with the primary image;
wherein the registering further comprises:
generating a deformation map representing anatomical differences between the primary image and the secondary image including transforms converting the primary image into the secondary image;
the method further including:
segmenting the secondary image into regions of interest by applying the deformation map transforms to previously segmented regions of interest in the primary image;
applying an auto-planning template previously generated for the primary image to the segmented regions of interest of the secondary image, the template including initial plan parameters and objectives; and reformulating the objectives including adding one or more additional objectives to the objectives by identifying a hot spot, and adding an objective corresponding to the identified hot spot to achieve a conformal dose distribution to target structures.

16. A therapy planning system for generating an optimal treatment plan, said system comprising:
at least one processor programmed to:
generate a first optimal treatment plan based on first imaging data of a subject using an auto-planning technique, the optimal treatment plan including dose delivery objectives and target structures;
control a delivery system to deliver therapy to the subject according to the optimal treatment plan and the dose delivery objectives over a period of time;
receive second imaging data of the same subject at the end of the period of time;
register the second imaging data with the first imaging data to generate a deformation map accounting for physiological changes in the second imaging data with respect to the first imaging data;
segment the second imaging data into regions of interest using the deformation map;
compute a mapped delivered dose for each region of interest using the dose delivery objectives of the first optimal treatment plan and the deformation map;
adding an additional dose delivery objective corresponding to an identified hot spot and adding an additional dose delivery objective corresponding to an identified cold spot, such that adding the additional dose delivery objectives corresponding to the identified hot and cold spots conforms the dose distribution to the target structures; and
generate a second optimal treatment plan based on the second imaging data and the segmented regions of interest.

* * * * *